United States Patent [19]

Sandler

[11] Patent Number: 5,294,743
[45] Date of Patent: Mar. 15, 1994

[54] PROCESS FOR THE TRANSFER OF ALKYL GROUPS IN DIALKYL TRISULFIDES AND MERCAPTANS

[75] Inventor: Stanley R. Sandler, Springfield, Pa.

[73] Assignee: Elf Atochem North America, Inc., Philadelphia, Pa.

[21] Appl. No.: 28,477

[22] Filed: Mar. 9, 1993

[51] Int. Cl.$^5$ .......................... C07C 319/22
[52] U.S. Cl. ........................ 568/26; 568/21
[58] Field of Search ................ 568/26, 21

[56] References Cited

U.S. PATENT DOCUMENTS 2,510,893 12/1946 Kleiman .................. 568/25
3,299,146 1/1967 Gilette et al. ............ 568/26

OTHER PUBLICATIONS

M. B. Evans et al., Proceedings Chemical Society, pp. 18–19 (1962).

*Primary Examiner*—Marianne M. Cintins
*Assistant Examiner*—Margaret J. Page

[57] ABSTRACT

The alkyl groups of dialkyl trisulfides are exchanged with the alkyl groups of mercaptans by reacting a tertiary dialkyl trisulfide with an alkyl mercaptan having a greater number of carbon atoms in its alkyl group than said trisulfide in the presence of an acidic or basic type catalyst for a time and a temperature sufficient to produce a dialkyl trisulfide having at least one transferred alkyl group from said mercaptan.

14 Claims, No Drawings

PROCESS FOR THE TRANSFER OF ALKYL GROUPS IN DIALKYL TRISULFIDES AND MERCAPTANS

BACKGROUND OF THE INVENTION

This invention concerns a process for the facile transfer of alkyl groups between dialkyltrisulfides and alkyl mercaptans. More particularly, it concerns the catalytically induced transfer of one or more tertiary alkyl groups between a di-tertiary alkyl trisulfide and a mercaptan having a higher alkyl group to thereby produce dialkyl trisulfides incorporating transferred alkyl groups and having utility as extreme pressure additives in lubricating compositions.

THE PRIOR ART

The reaction of ethyl mercaptan with diethyl trisulfide catalyzed by piperidine was reported in the literature [M. B. Evans and B. Saville, Proceedings Chem. Soc., 18–19 (1962)] to give two moles of diethyl disulfide and one mole of piperidinium hydrosulfide. These same authors also reported that isopropyl mercaptan reacted with 1,3-dimethylbut-2-enyl trisulfide in the presence of piperidine produced only traces of diisopropyl trisulfides and gave mainly 1,3-dimethylbut-2-enyl isopropyl disulfide, diisopropyl disulfide and 1,3-dimethylbut-2-ene-1-thiol per mole of initial trisulfide.

A related reaction was reported by L. A. Gillette and L. R. Martin in U.S. Pat. No. 3,299,146 wherein methyl mercaptan is reacted with dimethyl trisulfide in the presence of triethylamine catalyst to give dimethyl disulfide and hydrogen sulfide as shown below.

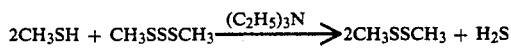

This prior art leads away from the present invention wherein mercaptans react with dialkyl trisulfides in the presence of basic catalysts, to give a variety of disulfides that incorporate the starting mercaptan alkyl moiety.

STATEMENT OF THE INVENTION

This invention is a process for the transfer of alkyl groups comprising reacting a di-tertiary $C_{4\text{-}12}$ alkyl trisulfide with a $C_{5\text{-}20}$ alkyl mercaptan where the mercaptan contains a greater number of carbon atoms than an alkyl group of the trisulfide, in the presence of an effective amount of an acidic or basic type catalyst at a temperature and for a time sufficient to produce a dialkyl trisulfide having at least one transferred alkyl group from said mercaptans. The invention also is in a composition of matter which is a mixture of asymmetric and symmetric dialkyl trisulfides.

DETAILED DESCRIPTION OF THE INVENTION

The process of this invention involves the transference of tertiary (t)-alkyl groups from a trisulfide reactant and an alkyl group from a mercaptan reactant. The trisulfide is a di-t-alkyl trisulfide or a di-t-alkyl higher sulfur rank polysulfide where the polysulfide may dissociate under the conditions of this reaction resulting in the presence of di-t-alkyl trisulfide. The alkyl groups of the trisulfide are t-alkyls having from 4 to 12 carbon atoms, preferably t-butyl, t-nonyl and t-dodecyl.

The mercaptan contains an alkyl group having from 5 to 20 carbons but for the purpose of this reaction will contain at least one more carbon atom than an alkyl group in the dialkyl trisulfide. Examples of the alkyl groups include pentyl, isopentyl, t-pentyl, hexyl, isohexyl, t-hexyl, heptyl, octyl, isoctyl, nonyl, t-nonyl, decyl, t-decyl, dodecyl, t-dodecyl, tetradecyl, pentadecyl, hexadecyl, octadecyl, eicocyl and alkyl isomers of these.

The product compounds which result from the process of this invention are mixtures of symmetrical and unsymmetrical trisulfides.

A general equation demonstrating the reaction is as follows:

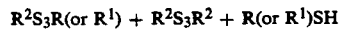

where one or both of R and $R^1$ are tertiary alkyl groups having from 4 to 12 carbon atoms and $R^2$ is an alkyl group having from 5 to 20 carbon atoms.

The catalysts for this invention are both acidic and basic types. The acidic type tends to produce more symmetrical products and a higher proportion of trisulfides. The basic catalysts tend to produce a greater amount of unsymmetric products. Examples of acidic-type catalysts include acidic ion-exchange materials of the resin and non-resin based type; organic acids, e.g., carboxylic and sulfonic acids; inorganic acids such as the mineral acids, phosphoric acid, phosphotungstic acid, silicotungstic acid, arsenic acid and Lewis Acids, such as boron trifluoride, aluminum chloride and zinc chloride. Preferably, the acid catalyst is one that is readily separated from the reaction mixture such as the acidic-ion exchange resins. A preferred catalyst of this type is Amberlyst ® 15, a strongly acidic, cation exchange resin of Rohm and Haas Co. having an —SO₃H functional structure and a macroreticular form. Other acidic ion exchange resins are available and include, for example, the Amberlite ® 200 series sold by Rohm and Haas and Dowex ® 50 sold by Dow Chemical Co.

Basic type catalysts include, for example, strongly and weakly basic, anion exchange resins and non resins, oxides and hydroxides of alkali and alkaline earth metals, other inorganic bases, ammonia and amines. Amines include, for example, alkyl, alkanol and aryl amines. The anion exchangers are the preferred basic catalysts of this invention and may have, for example, tertiary amine or quaternary ammonium functional groups attached to the base material. Examples of commercially available anion exchangers are Amberlyst ® A-21, a weakly basic anion exchange resin having tertiary amine functionality and consisting of macroreticular beads; Amberlite ® IRA-93, a weakly basic anion exchange resin containing tertiary amine functionality; Amberlite ® IRA 900 series, strongly basic anion exchange resins having quaternary ammonium functionality.

The catalyst is used in the process of this invention in effective amounts, i.e., amounts which will promote or increase the rate of the reaction. Preferably, the catalyst is heterogenous and is used in an amount ranging from about 60 to about 105g for each mol of trisulfide or mercaptan. It is also preferred that the catalyst be dry or anhydrous to obtain higher activity. The catalyst may be easily separated and reused in other preparations.

The reaction temperature utilized is that at which the alkyl transfer reaction occurs and is generally between about 50° and 150° C., preferably between about 80° and about 120° C.

The pressure of the reaction is not critical but will generally be from about atmospheric up to about 1000 psig, preferably from about 0 to 100 psig.

The reaction time is that over which the desired alkyl transfer reaction occurs under the temperature and pressure of the reaction. Generally, for a batch reaction, a time period ranging from about 1 hour to about 24 hours is employed. Preferably, a time of from about 1 hour and about 8 hours will be sufficient for the reaction.

The dialkyl trisulfide and alkyl mercaptan reactants are generally used at a mole ratio of from about 1:1 to about 1:10 depending on the product desired. For a weight majority of unsymmetrical trisulfide in the product a ratio of from about 1:1 to about 1:1.2 of starting reactants are used. Where it is desired to prepare a majority of symmetrical trisulfide in the product, a mole ratio of from about 1:2 to about 1:6 of trisulfide to mercaptan is used.

The reaction is carried out as either a batch process or as a continuous process wherein the reactants and products are depicted in the following equation:

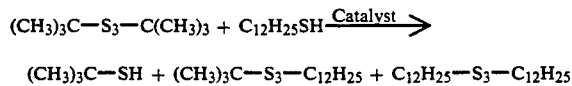

$$(CH_3)_3C-SH + (CH_3)_3C-S_3-C_{12}H_{25} + C_{12}H_{25}-S_3-C_{12}H_{25}$$

The composition of matter resulting from the process of this invention is a mixture comprising from 5 to 95 percent based on the weight of the mixture of an unsymmetrical dialkyl trisulfide where one alkyl group is a tertiary alkyl having from 4 to 12 carbons and the other alkyl has from 5 to 20 carbons, and from 95 to 5 percent, based on the weight of the mixture of a symmetrical dialkyl trisulfide where the alkyl groups each have from 5 to 20 carbons.

The following examples are set forth to demonstrate the merits of this invention.

Example 1

Basic Catalyst

To a reactor was added 0.39g (0.002 mole) of a di-t-butyl trisulfide, 0.39g (0.0019 mole) of n-dodecyl mercaptan and 0.160 of Amberlyst ® A-21 catalyst (tertiary amine functionality-weakly basic ion-exchange resin from Rohm & Haas Co.). The mixture was warmed at 80°-90° C. and occasionally shaken during about 12 hours to give a significant amount of reaction in which the GC area% of unsymmetrical/symmetrical trisulfides was about 12/1.

The crude reaction mixture was run on GC and indicated 27.2% $(CH_3)_3$ C-$S_3$-C$(CH_3)_3$, 12.9 % n-$C_{12}H_{25}$-SH, 36.6 % n-$C_{12}H_{25}$-$S_3$-C$(CH_3)_3$, 3.2% n-$C_{12}H_{25}$-$S_3$-n-$CH_{12}H_{25}$ and about 12.5% of a low boiler [$(CH_3)_3$ C-SH]:

Example 2

Acidic Catalyst

To a reactor was added 0.210g (0.001 mole) of di-t-butyl trisulfide, 0.23g (0.0011 mole) of n-dodecyl mercaptan and 0.170g Amberlyst ® 15 (dried) catalyst. The mixture was warmed at 80°-90° C. and occasionally shaken for about 5½ hours to give a significant amount of reaction in which the GC area% was 7.2% of n-$C_{12}H_{25}$-$S_3$-C$(CH_3)_3$, 9.8% n-$C_{12}$-$H_{25}$-$S_3$-n-$C_{12}H_{25}$, 15.8% $(CH_3)_3$ C-$S_3$-C$(CH_3)_3$ and 19.9% n-$C_{12}H_{25}$-SH along with low boiler to make up the balance (low boiler is believed to be t-butyl mercaptan).

Comparative Example

No Catalyst

To a reactor was added 0.210g (0.001 mole) of di-t-butyl trisulfide and 0.24g (0.0012 mole) of n-dodecylmercaptan. The mixture was warmed at 80°-90° C. and occasionally shaken from about 12 hours to give no significant amount of reaction as determined by gas chromatography (GC).

The advantage of this process is that it allows one the ability to prepare trisulfides, especially unsymmetrical trisulfides, free of large amounts of the corrosive (to metals) tetrasulfides. The clean transfer of the trisulfide ("$S_3$") group is unexpected in view of the prior art processes as disclosed in the Background of the Invention section.

A commercial value of this invention is that mixed trisulfides such as $C_4$-$S_3$-$C_9$ can be prepared which may have improved utility for lubricant additive applications. Other higher molecular weight trisulfides can be prepared by this process without having significant quantities of di and polysulfides as contamination. In general, the lubricant industry desires the use of both symmetrical and unsymmetrical trisulfides to replace the environmentally objectionable (due to presence of chlorine) sulfurized isobutylenes.

I claim:

1. A process for the transfer of alkyl groups comprising reacting a tertiary di-$C_{4-12}$ alkyltrisulfide with a $C_{5-20}$ alkyl mercaptan where the mercaptan contains a greater number of carbon atoms than an alkyl group on said trisulfide, in the presence of an effective amount of an acidic type catalyst at a temperature and for a time sufficient to produce a dialkyl trisulfide having at least one transferred alkyl group from said mercaptan.

2. The process of claim 1 wherein said di-$C_{4-12}$ alkyl trisulfide is a di-tertiary butyl, di-tertiary nonyl or di-tertiary dodecyl trisulfide.

3. The process of claim 1 wherein said di-$C_{4-12}$ alkyl trisulfide is a symmetrical alkyl trisulfide.

4. The process of claim 1 wherein said $C_{5-20}$ alkyl mercaptan is tertiary alkyl mercaptan.

5. The process of claim 1 wherein the acidic type catalyst is a strongly acidic cation exchange resin having an —$SO_3H$ functional structure.

6. The process of claim 1 wherein the mole ratio of trisulfide to mercaptan is form about 1:2 to about 1:6.

7. The process of claim 1 wherein the reaction is conducted at a temperature ranging from about 50° to about 150° C.

8. The process of claim 7 wherein the reaction is conducted at a pressure of between about atmospheric and about 1000 psig.

9. The process of claim 8 wherein the mole ratio of trisulfide to mercaptan is from 1:1 to 1:10.

10. A process for the transfer of alkyl groups comprising reacting a di-tertiary butyl, di-tertiary nonyl or di-tertiary dodecyl trisulfide with a $C_{5-20}$ alkyl mercaptan where the mercaptan contains a greater number of carbon atoms than a tertiary alkyl group of said trisulfide in a mole ratio of trisulfide to mercaptan ranging from 1:1 to 1:10, at a temperature ranging from about 50° to about 150° C., at a pressure of between about atmospheric and 1000 psig, in the presence of an acidic cation exchange resin or a basic anion exchange resin in an effective catalytic amount, and for a time of between about 1 and about 8 hours.

11. The process of claim 10 where the mole ratio of trisulfide to mercaptan is about 1:1 to about 1:1.2.

12. The process of claim 11 where the catalyst is a basic anion exchange resin.

13. The process of claim 10 where the mole ratio of trisulfide to mercaptan is about 1.2 to about 1:6.

14. The process of claim 13 where the catalyst is an acidic cation exchange resin.

* * * * *